United States Patent
Rothe et al.

(10) Patent No.: US 9,220,402 B2
(45) Date of Patent: *Dec. 29, 2015

(54) VISUALIZATION AND TREATMENT VIA PERCUTANEOUS METHODS AND DEVICES

(75) Inventors: Chris A. Rothe, San Mateo, CA (US); Vahid Saadat, Atherton, CA (US); Kevin H. Van Bladel, Livermore, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/810,850

(22) Filed: Jun. 7, 2007

(65) Prior Publication Data
US 2009/0082623 A1 Mar. 26, 2009

Related U.S. Application Data

(60) Provisional application No. 60/804,168, filed on Jun. 7, 2006.

(51) Int. Cl.

| A61B 1/00 | (2006.01) |
|---|---|
| A61B 1/04 | (2006.01) |
| A61B 1/06 | (2006.01) |
| A61B 6/00 | (2006.01) |
| A61B 18/18 | (2006.01) |
| A61B 1/313 | (2006.01) |
| A61B 17/00 | (2006.01) |
| A61B 17/064 | (2006.01) |

(52) U.S. Cl.
CPC ............ *A61B 1/3137* (2013.01); *A61B 1/00082* (2013.01); *A61B 1/00089* (2013.01); *A61B 1/00147* (2013.01); *A61B 17/0057* (2013.01); *A61B 17/064* (2013.01); *A61B 2017/0061* (2013.01); *A61B 2017/00243* (2013.01); *A61B 2017/00579* (2013.01); *A61B 2017/00592* (2013.01); *A61B 2017/00597* (2013.01); *A61B 2017/00615* (2013.01); *A61B 2017/00623* (2013.01); *A61B 2017/0641* (2013.01)

(58) Field of Classification Search
CPC ............ A61B 1/0008; A61B 1/00082; A61B 1/00087; A61B 1/00089; A61B 1/00096; A61B 1/32; A61B 1/63; A61B 18/24; A61B 18/245; A61B 18/22; A61B 18/1492; A61M 29/00
USPC ......... 600/104, 109, 160, 106, 114–116, 121, 600/127, 129, 175, 476; 606/15, 42, 191, 606/197–200; 607/23.72; 604/96.01, 604/97.01–97.03, 98.01–98.02, 104–109
See application file for complete search history.

(56) References Cited

U.S. PATENT DOCUMENTS

| 3,874,388 A | 4/1975 | King et al. | |
|---|---|---|---|
| 4,681,093 A * | 7/1987 | Ono et al. | 600/116 |

(Continued)

*Primary Examiner* — Ryan Henderson

(57) ABSTRACT

Visualization and treatment of tissue regions via percutaneous access methods and devices are described herein. The system may include a deployment catheter and an expandable imaging hood. In use, the hood may be introduced from outside the patient body through a percutaneous incision and advanced through a subxiphoid pathway, for example, to the heart where entry may be accomplished via an incision through the left atrial appendage. Once within the heart, the hood can be advanced to any chamber to visualize and/or treat tissue by placing the hood against the tissue to be imaged and pumping translucent fluids into the hood until the fluid displaces any blood, thereby leaving a clear region of tissue to be imaged via an imaging element in the deployment catheter. Additionally, any number of therapeutic tools can also be passed through the deployment catheter and into the imaging hood for treating the tissue of interest.

35 Claims, 26 Drawing Sheets

(56) References Cited

U.S. PATENT DOCUMENTS

| | | | | |
|---|---|---|---|---|
| 4,961,738 | A | * | 10/1990 | Mackin ............................ 606/15 |
| 5,823,947 | A | * | 10/1998 | Yoon et al. .................... 600/207 |
| 7,398,781 | B1 | * | 7/2008 | Chin ............................. 128/898 |
| 2004/0117032 | A1 | * | 6/2004 | Roth .......................... 623/23.72 |
| 2005/0119523 | A1 | * | 6/2005 | Starksen et al. .............. 600/109 |
| 2005/0131401 | A1 | * | 6/2005 | Malecki et al. ................. 606/27 |
| 2005/0182465 | A1 | | 8/2005 | Ness |
| 2006/0184048 | A1 | | 8/2006 | Saadat |

* cited by examiner

VISUALIZATION AND TREATMENT VIA PERCUTANEOUS METHODS AND DEVICES

CROSS-REFERENCE TO RELATED APPLICATIONS

This application claims the benefit of priority to U.S. Prov. Pat. App. Ser. No. 60/804,168 filed Jun. 7, 2006, which is incorporated herein by reference in its entirety.

FIELD OF THE INVENTION

The present invention relates generally to medical devices used for visualizing and/or manipulating regions of tissue within a body. More particularly, the present invention relates to apparatus and methods for visualizing and/or manipulating tissue regions within a body lumen, e.g., tissue within a heart, by accessing the body lumen via percutaneous approaches particularly through a left atrial appendage.

BACKGROUND OF THE INVENTION

Conventional devices for visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

Thus, a tissue imaging system which is able to provide real-time in vivo images of tissue regions within body lumens such as the heart, which are accessed via percutaneous methods and devices, through opaque media such as blood and which also provide instruments for therapeutic procedures upon the visualized tissue are desirable.

BRIEF SUMMARY OF THE INVENTION

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

The imaging hood may be formed into any number of configurations and the imaging assembly may also be utilized with any number of therapeutic tools which may be deployed through the deployment catheter.

Moreover, access to the body lumen, such as within the heart, may be achieved through percutaneous methods and devices. For instance, an imaging assembly may be advanced through a percutaneous incision into the patient body. Another incision may be made through the surface of a region of tissue, such as the left atrial appendage, and the instrument may be advanced from outside the heart and into the left atrial chamber via the left atrial appendage incision to effect various procedures within the heart.

Once within the heart, the instrument may be manipulated and steered to access any of the other chambers within the heart to affect any number of procedures, such as closure of a septal defect, removal of emboli, treatment of atrial fibrillation, etc.

DETAILED DESCRIPTION OF THE INVENTION

A tissue-imaging and manipulation apparatus described below is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating trans-septal access to the left atrium, cannulating the coronary sinus, diagnosis of valve regurgitation/stenosis, valvuloplasty, atrial appendage closure, arrhythmogenic focus ablation, among other procedures. Details of tissue imaging and manipulation systems and methods which may be utilized with apparatus and methods described herein are described in U.S. patent application Ser. No. 11/259,498 filed Oct. 25, 2005 (U.S. Pat. Pub. No. 2006/0184048 A1), which is incorporated herein by reference in its entirety.

Figure 1A:
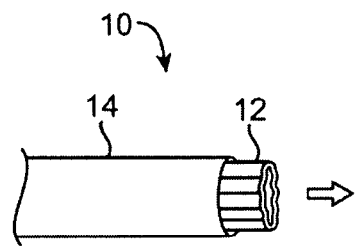
FIG. 1A shows a side view of one variation of a tissue imaging apparatus during deployment from a sheath or delivery catheter.
Figure 1B:
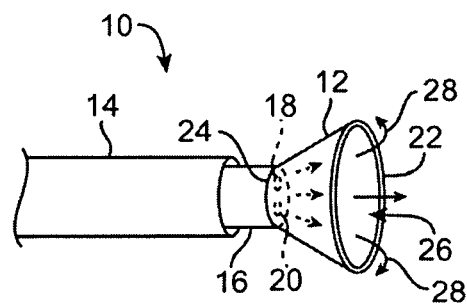
FIG. 1B shows the deployed tissue imaging apparatus of FIG. 1A having an optionally expandable hood or sheath attached to an imaging and/or diagnostic catheter.
Figure 1C:
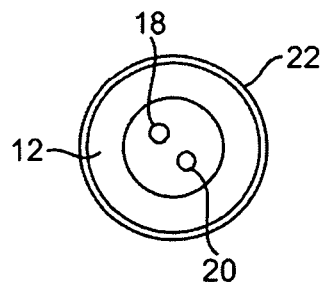
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, such as the mitral valve located at the outflow tract of the left atrium of the heart, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a trans-septal procedure or septostomy. For procedures such as percutaneous valve repair and replacement, trans-septal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, Del.), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 1D:
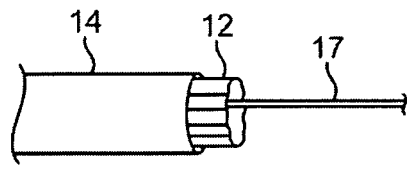
FIGS. 1D to 1F show the apparatus of FIGS. 1A to 1C with an additional lumen, e.g., for passage of a guidewire therethrough.
Figure 1E:
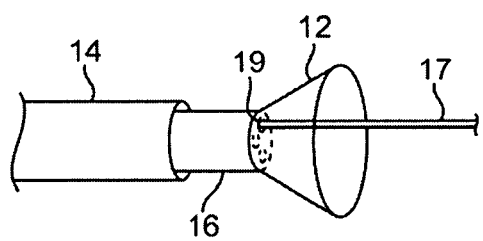
Figure 1F:
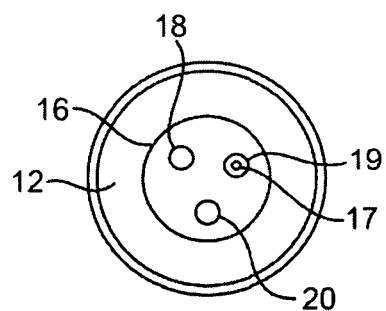

The imaging and manipulation assembly 10 may additionally define a guidewire lumen therethrough, e.g., a concentric or eccentric lumen, as shown in the side and end views, respectively, of FIGS. 1D to 1F. The deployment catheter 16 may define guidewire lumen 19 for facilitating the passage of the system over or along a guidewire 17, which may be advanced intravascularly within a body lumen. The deployment catheter 16 may then be advanced over the guidewire 17, as generally known in the art.

In operation, after imaging hood 12 has been deployed, as in FIG. 1B, and desirably positioned against the tissue region to be imaged along contact edge 22, the displacing fluid may be pumped at positive pressure through fluid delivery lumen 18 until the fluid fills open area 26 completely and displaces any fluid 28 from within open area 26. The displacing fluid flow may be laminarized to improve its clearing effect and to help prevent blood from re-entering the imaging hood 12. Alternatively, fluid flow may be started before the deployment takes place. The displacing fluid, also described herein as imaging fluid, may comprise any biocompatible fluid, e.g., saline, water, plasma, etc., which is sufficiently transparent to allow for relatively undistorted visualization through the fluid. Alternatively or additionally, any number of therapeutic drugs may be suspended within the fluid or may comprise the fluid itself which is pumped into open area 26 and which is subsequently passed into and through the heart and the patient body.

Figure 2A:
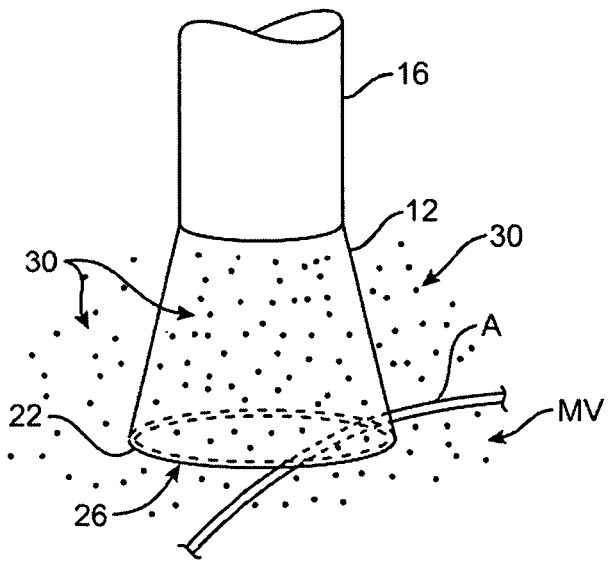
FIGS. 2A and 2B show one example of a deployed tissue imager positioned against or adjacent to the tissue to be imaged and a flow of fluid, such as saline, displacing blood from within the expandable hood.
Figure 2B:
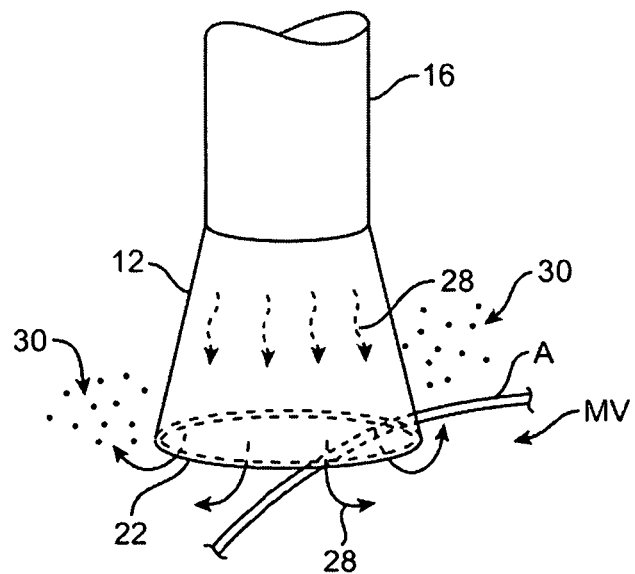

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
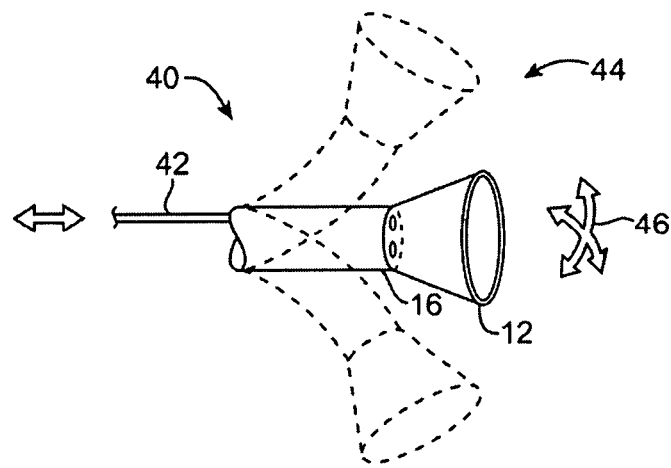
FIG. 3A shows an articulatable imaging assembly which may be manipulated via push-pull wires or by computer control.

In desirably positioning the assembly at various regions within the patient body, a number of articulation and manipulation controls may be utilized. For example, as shown in the articulatable imaging assembly 40 in FIG. 3A, one or more push-pull wires 42 may be routed through deployment catheter 16 for steering the distal end portion of the device in various directions 46 to desirably position the imaging hood 12 adjacent to a region of tissue to be visualized. Depending upon the positioning and the number of push-pull wires 42 utilized, deployment catheter 16 and imaging hood 12 may be articulated into any number of configurations 44. The push-pull wire or wires 42 may be articulated via their proximal ends from outside the patient body manually utilizing one or more controls. Alternatively, deployment catheter 16 may be articulated by computer control, as further described below.

Figure 3B:
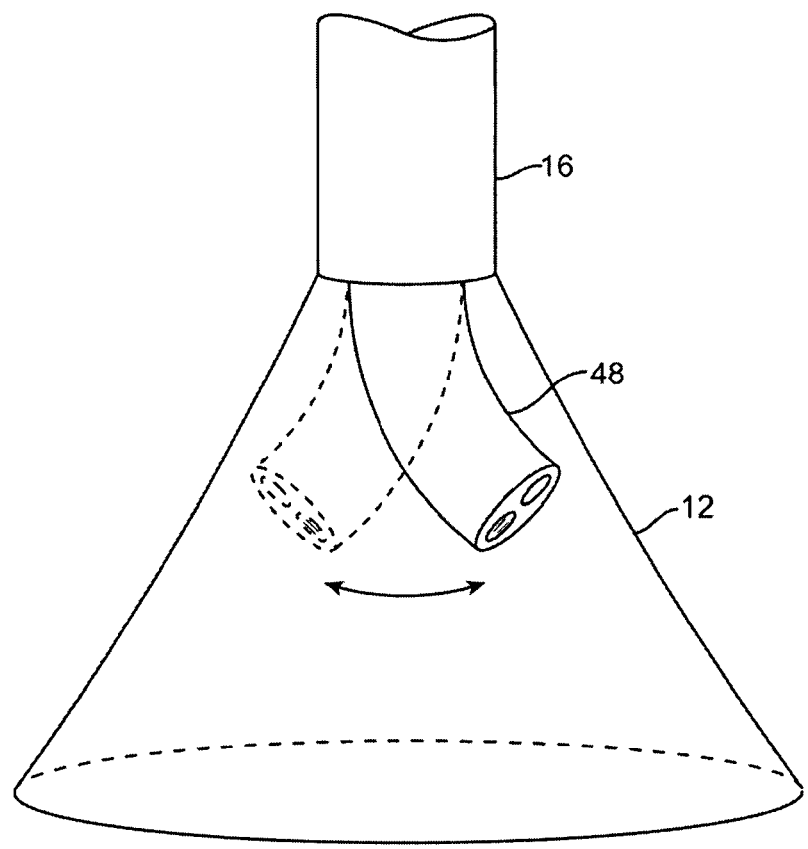
FIGS. 3B and 3C show steerable instruments, respectively, where an articulatable delivery catheter may be steered within the imaging hood or a distal portion of the deployment catheter itself may be steered.

Additionally or alternatively, an articulatable delivery catheter 48, which may be articulated via one or more push-pull wires and having an imaging lumen and one or more working lumens, may be delivered through the deployment catheter 16 and into imaging hood 12. With a distal portion of articulatable delivery catheter 48 within imaging hood 12, the clear displacing fluid may be pumped through delivery catheter 48 or deployment catheter 16 to clear the field within imaging hood 12. As shown in FIG. 3B, the articulatable delivery catheter 48 may be articulated within the imaging hood to obtain a better image of tissue adjacent to the imaging hood 12. Moreover, articulatable delivery catheter 48 may be articulated to direct an instrument or tool passed through the catheter 48, as described in detail below, to specific areas of tissue imaged through imaging hood 12 without having to reposition deployment catheter 16 and re-clear the imaging field within hood 12.

Figure 3C:
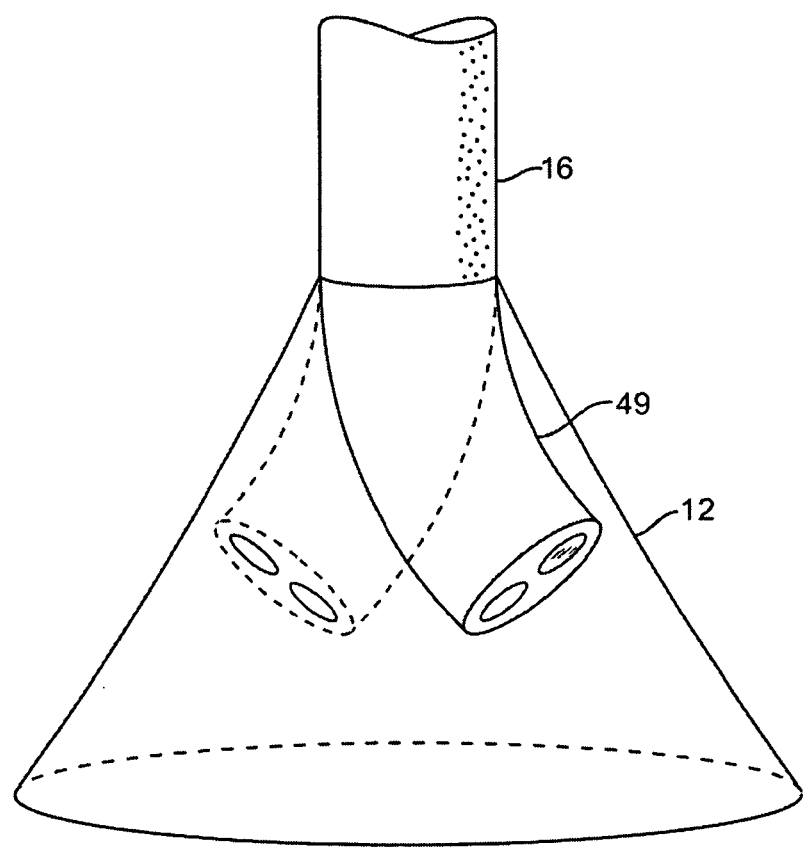

Alternatively, rather than passing an articulatable delivery catheter 48 through the deployment catheter 16, a distal portion of the deployment catheter 16 itself may comprise a distal end 49 which is articulatable within imaging hood 12, as shown in FIG. 3C. Directed imaging, instrument delivery, etc., may be accomplished directly through one or more lumens within deployment catheter 16 to specific regions of the underlying tissue imaged within imaging hood 12.

Figure 4A:
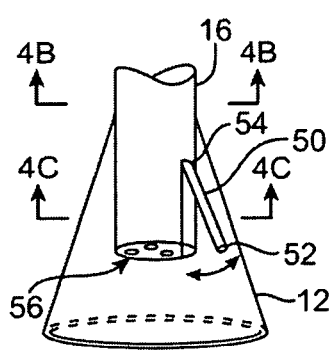
FIGS. 4A to 4C show side and cross-sectional end views, respectively, of another variation having an off-axis imaging capability.

Visualization within the imaging hood 12 may be accomplished through an imaging lumen 20 defined through deployment catheter 16, as described above. In such a configuration, visualization is available in a straight-line manner, i.e., images are generated from the field distally along a longitudinal axis defined by the deployment catheter 16. Alternatively or additionally, an articulatable imaging assembly having a pivotable support member 50 may be connected to, mounted to, or otherwise passed through deployment catheter 16 to provide for visualization off-axis relative to the longitudinal axis defined by deployment catheter 16, as shown in FIG. 4A. Support member 50 may have an imaging element 52, e.g., a CCD or CMOS imager or optical fiber, attached at its distal end with its proximal end connected to deployment catheter 16 via a pivoting connection 54.

Figure 4B:
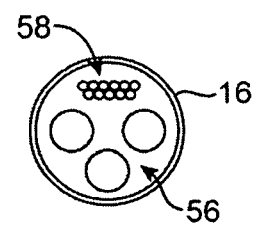
Figure 4C:
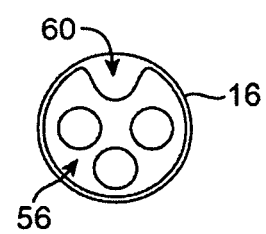

If one or more optical fibers are utilized for imaging, the optical fibers 58 may be passed through deployment catheter 16, as shown in the cross-section of FIG. 4B, and routed through the support member 50. The use of optical fibers 58 may provide for increased diameter sizes of the one or several lumens 56 through deployment catheter 16 for the passage of diagnostic and/or therapeutic tools therethrough. Alternatively, electronic chips, such as a charge coupled device (CCD) or a CMOS imager, which are typically known, may be utilized in place of the optical fibers 58, in which case the electronic imager may be positioned in the distal portion of the deployment catheter 16 with electric wires being routed proximally through the deployment catheter 16. Alternatively, the electronic imagers may be wirelessly coupled to a receiver for the wireless transmission of images. Additional optical fibers or light emitting diodes (LEDs) can be used to provide lighting for the image or operative theater, as described below in further detail. Support member 50 may be pivoted via connection 54 such that the member 50 can be positioned in a low-profile configuration within channel or groove 60 defined in a distal portion of catheter 16, as shown in the cross-section of FIG. 4C. During intravascular delivery of deployment catheter 16 through the patient body, support member 50 can be positioned within channel or groove 60 with imaging hood 12 also in its low-profile configuration. During visualization, imaging hood 12 may be expanded into its deployed configuration and support member 50 may be deployed into its off-axis configuration for imaging the tissue adjacent to hood 12, as in FIG. 4A. Other configurations for support member 50 for off-axis visualization may be utilized, as desired.

Figure 5A:
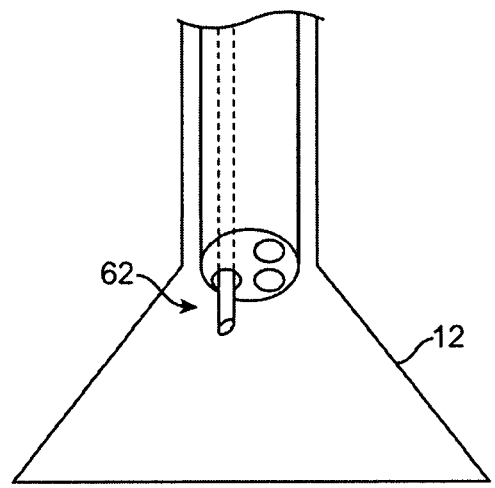
FIGS. 5A and 5B show examples of various visualization imagers which may be utilized within or along the imaging hood.
Figure 5B:
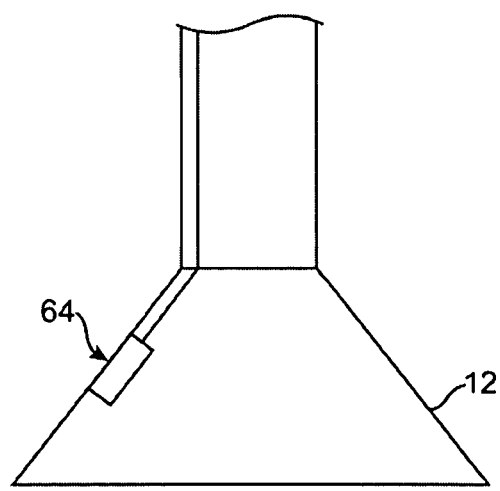

FIG. 5A shows a partial cross-sectional view of an example where one or more optical fiber bundles 62 may be positioned within the catheter and within imaging hood 12 to provide direct in-line imaging of the open area within hood 12. FIG. 5B shows another example where an imaging element 64 (e.g., CCD or CMOS electronic imager) may be placed along an interior surface of imaging hood 12 to provide imaging of the open area such that the imaging element 64 is off-axis relative to a longitudinal axis of the hood 12. The off-axis position of element 64 may provide for direct visualization and uninhibited access by instruments from the catheter to the underlying tissue during treatment.

Figure 6A:
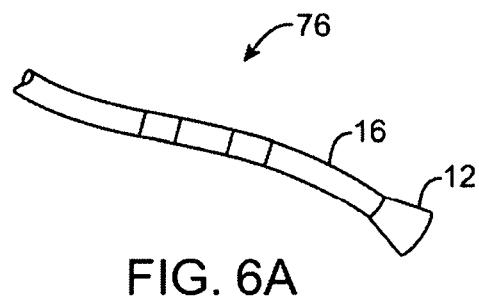
FIGS. 6A to 6C illustrate deployment catheters having one or more optional inflatable balloons or anchors for stabilizing the device during a procedure.
Figure 6B:
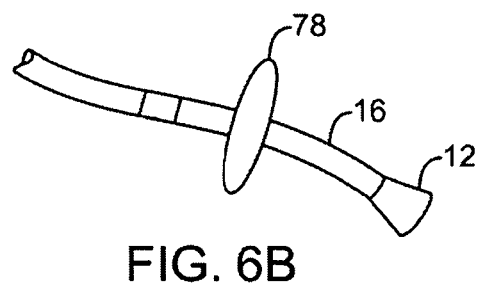
Figure 6C:
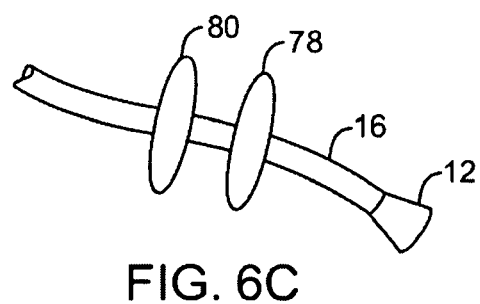

To facilitate stabilization of the deployment catheter 16 during a procedure, one or more inflatable balloons or anchors 76 may be positioned along the length of catheter 16, as shown in FIG. 6A. For example, when utilizing a transseptal approach across the atrial septum AS into the left atrium LA, the inflatable balloons 76 may be inflated from a low-profile into their expanded configuration to temporarily anchor or stabilize the catheter 16 position relative to the heart H. FIG. 6B shows a first balloon 78 inflated while FIG. 6C also shows a second balloon 80 inflated proximal to the first balloon 78. In such a configuration, the septal wall AS may be wedged or sandwiched between the balloons 78, 80 to temporarily stabilize the catheter 16 and imaging hood 12. A single balloon 78 or both balloons 78, 80 may be used. Other, alternatives may utilize expandable mesh members, malecots, or any other temporary expandable structure. After a procedure has been accomplished, the balloon assembly 76 may be deflated or re-configured into a low-profile for removal of the deployment catheter 16.

Figure 7A:
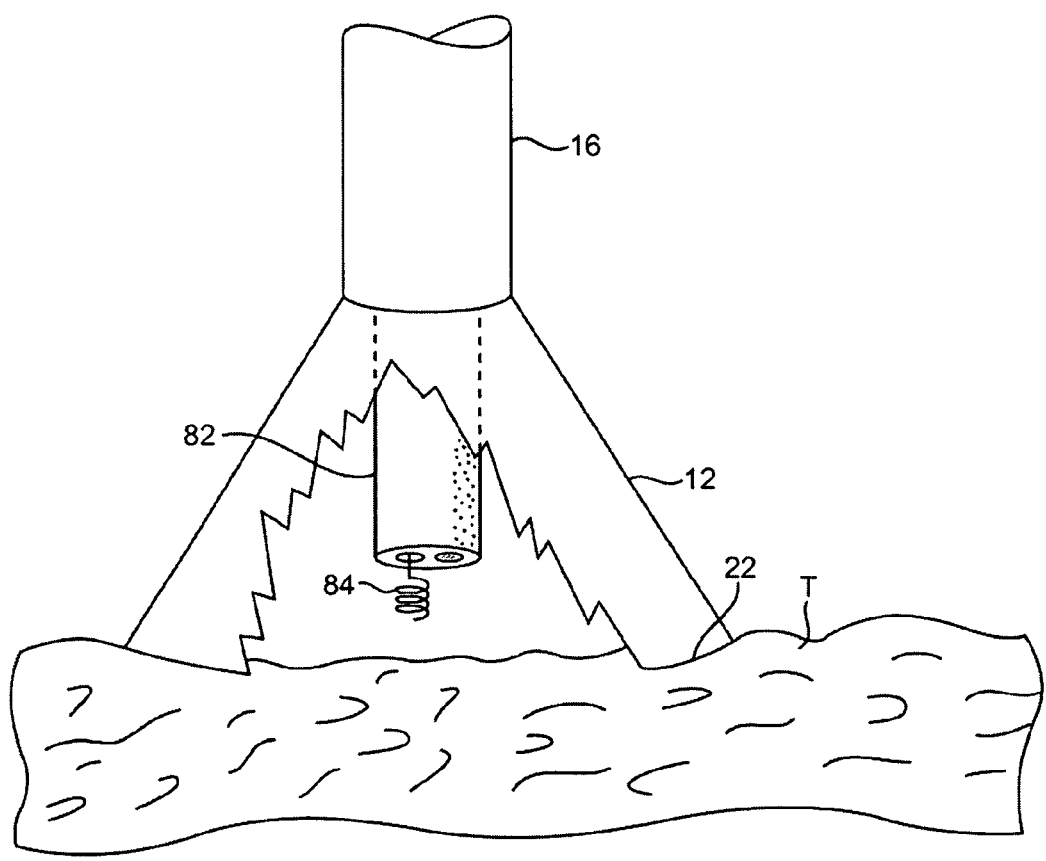
FIGS. 7A and 7B illustrate a variation of an anchoring mechanism such as a helical tissue piercing device for temporarily stabilizing the imaging hood relative to a tissue surface.

To further stabilize a position of the imaging hood 12 relative to a tissue surface to be imaged, various anchoring mechanisms may be optionally employed for temporarily holding the imaging hood 12 against the tissue. Such anchoring mechanisms may be particularly useful for imaging tissue which is subject to movement, e.g., when imaging tissue within the chambers of a beating heart. A tool delivery catheter 82 having at least one instrument lumen and an optional visualization lumen may be delivered through deployment catheter 16 and into an expanded imaging hood 12. As the imaging hood 12 is brought into contact against a tissue surface T to be examined, an anchoring mechanisms such as a helical tissue piercing device 84 may be passed through the tool delivery catheter 82, as shown in FIG. 7A, and into imaging hood 12.

Figure 7B:
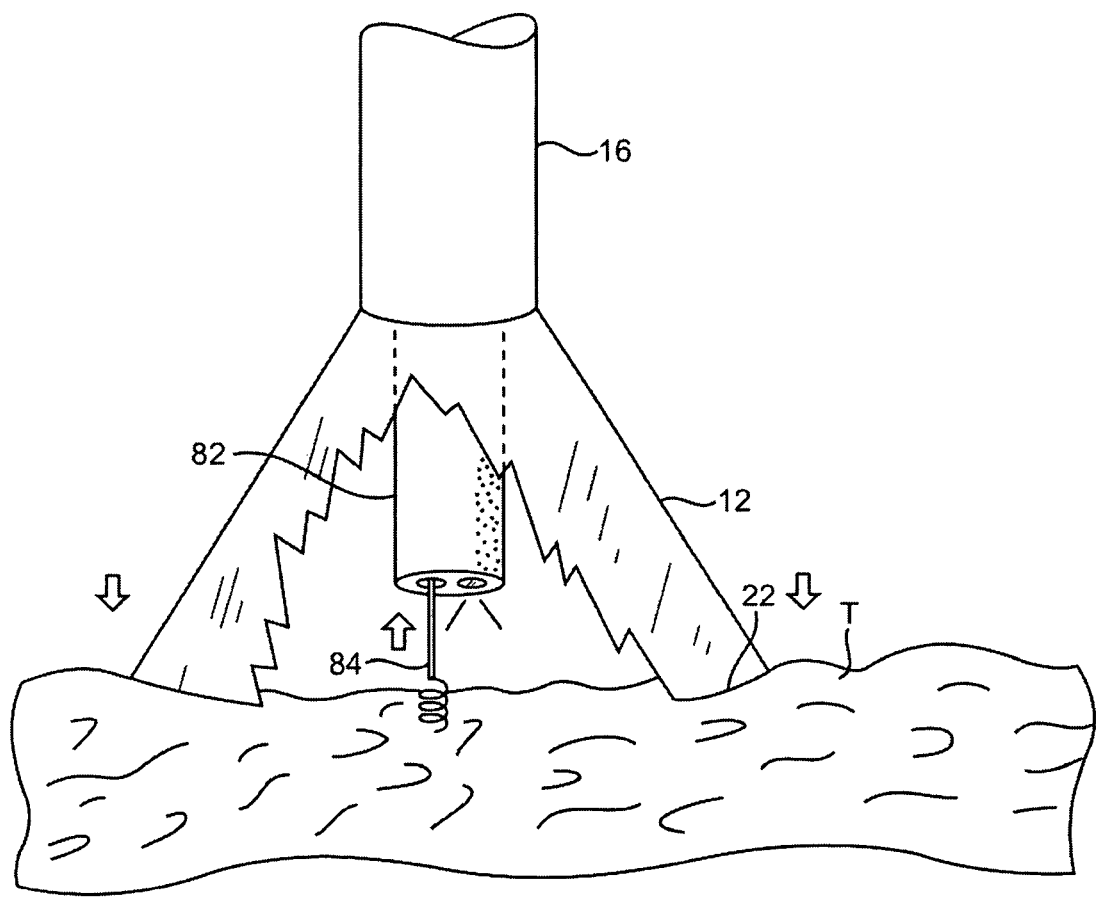

The helical tissue engaging device 84 may be torqued from its proximal end outside the patient body to temporarily anchor itself into the underlying tissue surface T. Once embedded within the tissue T, the helical tissue engaging device 84 may be pulled proximally relative to deployment catheter 16 while the deployment catheter 16 and imaging hood 12 are pushed distally, as indicated by the arrows in FIG. 7B, to gently force the contact edge or lip 22 of imaging hood against the tissue T. The positioning of the tissue engaging device 84 may be locked temporarily relative to the deployment catheter 16 to ensure secure positioning of the imaging hood 12 during a diagnostic or therapeutic procedure within the imaging hood 12. After a procedure, tissue engaging device 84 may be disengaged from the tissue by torquing its proximal end in the opposite direction to remove the anchor form the tissue T and the deployment catheter 16 may be repositioned to another region of tissue where the anchoring process may be repeated or removed from the patient body. The tissue engaging device 84 may also be constructed from other known tissue engaging devices such as vacuum-assisted engagement or grasper-assisted engagement tools, among others.

Although a helical anchor 84 is shown, this is intended to be illustrative and other types of temporary anchors may be utilized, e.g., hooked or barbed anchors, graspers, etc. Moreover, the tool delivery catheter 82 may be omitted entirely and the anchoring device may be delivered directly through a lumen defined through the deployment catheter 16.

Figure 7C:
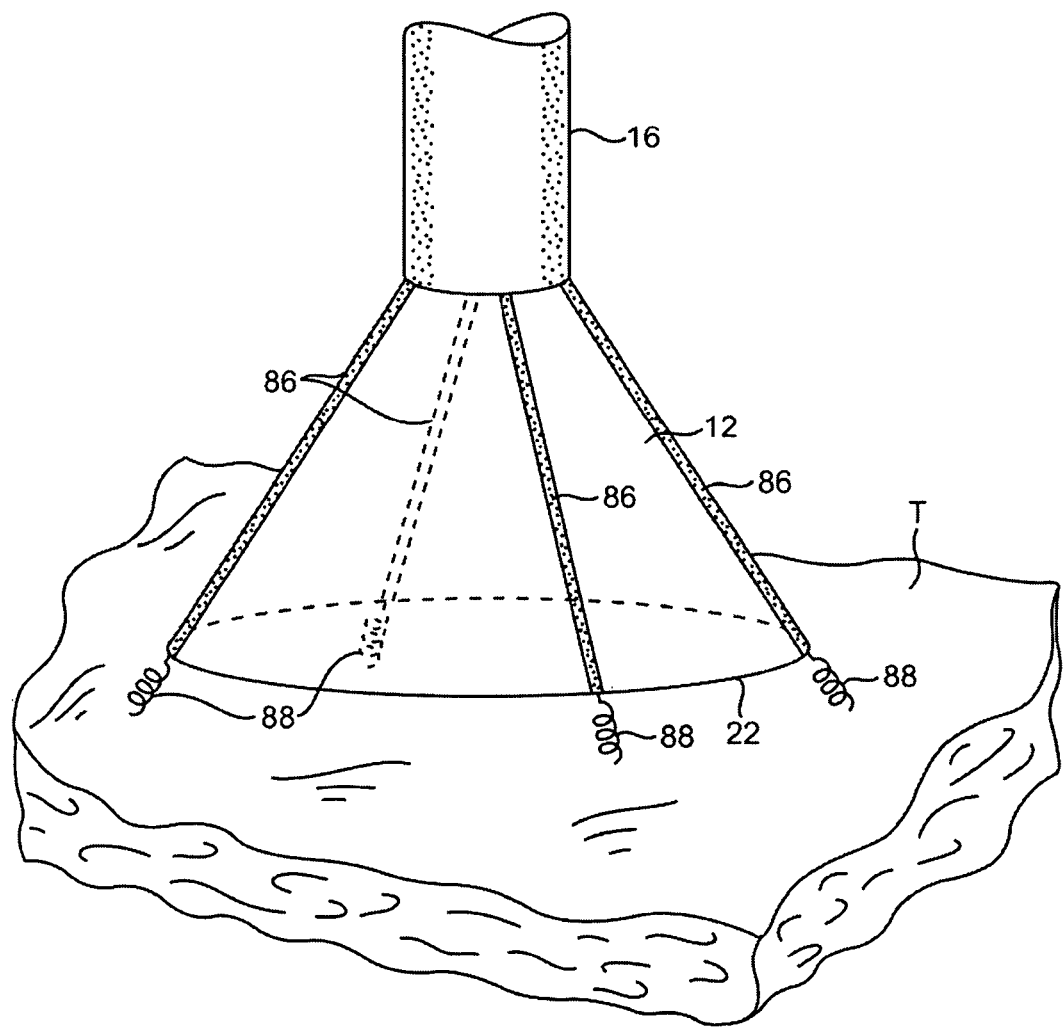
FIG. 7C shows another variation for anchoring the imaging hood having one or more tubular support members integrated with the imaging hood; each support members may define a lumen therethrough for advancing a helical tissue anchor within.

In another variation where the tool delivery catheter 82 may be omitted entirely to temporarily anchor imaging hood 12, FIG. 7C shows an imaging hood 12 having one or more tubular support members 86, e.g., four support members 86 as shown, integrated with the imaging hood 12. The tubular support members 86 may define lumens therethrough each having helical tissue engaging devices 88 positioned within. When an expanded imaging hood 12 is to be temporarily anchored to the tissue, the helical tissue engaging devices 88 may be urged distally to extend from imaging hood 12 and each may be torqued from its proximal end to engage the underlying tissue T. Each of the helical tissue engaging devices 88 may be advanced through the length of deployment catheter 16 or they may be positioned within tubular support members 86 during the delivery and deployment of imaging hood 12. Once the procedure within imaging hood 12 is finished, each of the tissue engaging devices 88 may be disengaged from the tissue and the imaging hood 12 may be repositioned to another region of tissue or removed from the patient body.

Figure 8A:
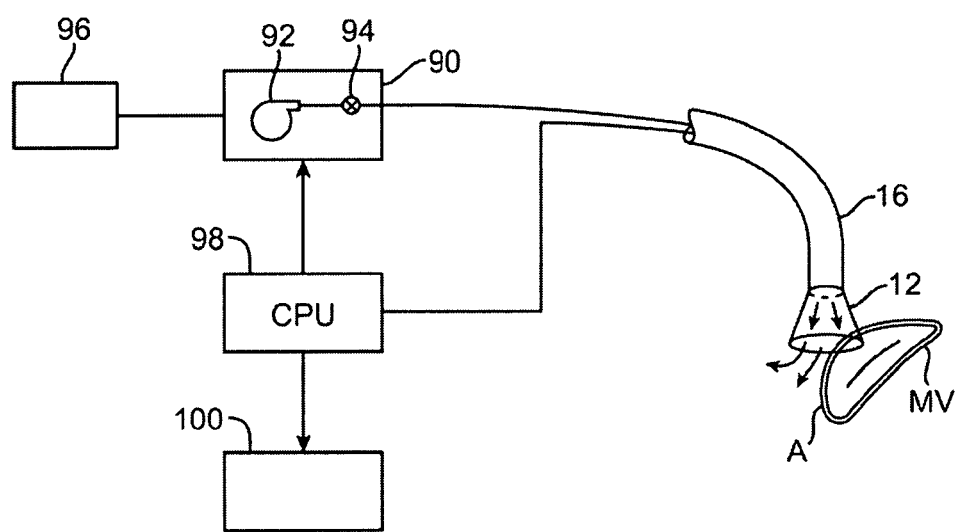
FIG. 8A shows an illustrative example of one variation of how a tissue imager may be utilized with an imaging device.

An illustrative example is shown in FIG. 8A of a tissue imaging assembly connected to a fluid delivery system 90 and to an optional processor 98 and image recorder and/or viewer 100. The fluid delivery system 90 may generally comprise a pump 92 and an optional valve 94 for controlling the flow rate of the fluid into the system. A fluid reservoir 96, fluidly connected to pump 92, may hold the fluid to be pumped through imaging hood 12. An optional central processing unit or processor 98 may be in electrical communication with fluid delivery system 90 for controlling flow parameters such as the flow rate and/or velocity of the pumped fluid. The processor 98 may also be in electrical communication with an image recorder and/or viewer 100 for directly viewing the images of tissue-received from within imaging hood 12. Imager recorder and/or viewer 100 may also be used not only to record the image but also the location of the viewed tissue region, if so desired.

Optionally, processor 98 may also be utilized to coordinate the fluid flow and the image capture. For instance, processor 98 may be programmed to provide for fluid flow from reservoir 96 until the tissue area has been displaced of blood to obtain a clear image. Once the image has been determined to be sufficiently clear, either visually by a practitioner or by computer, an image of the tissue may be captured automatically by recorder 100 and pump 92 may be automatically stopped or slowed by processor 98 to cease the fluid flow into the patient. Other variations for fluid delivery and image capture are, of course, possible and the aforementioned configuration is intended only to be illustrative and not limiting.

Figure 8B:
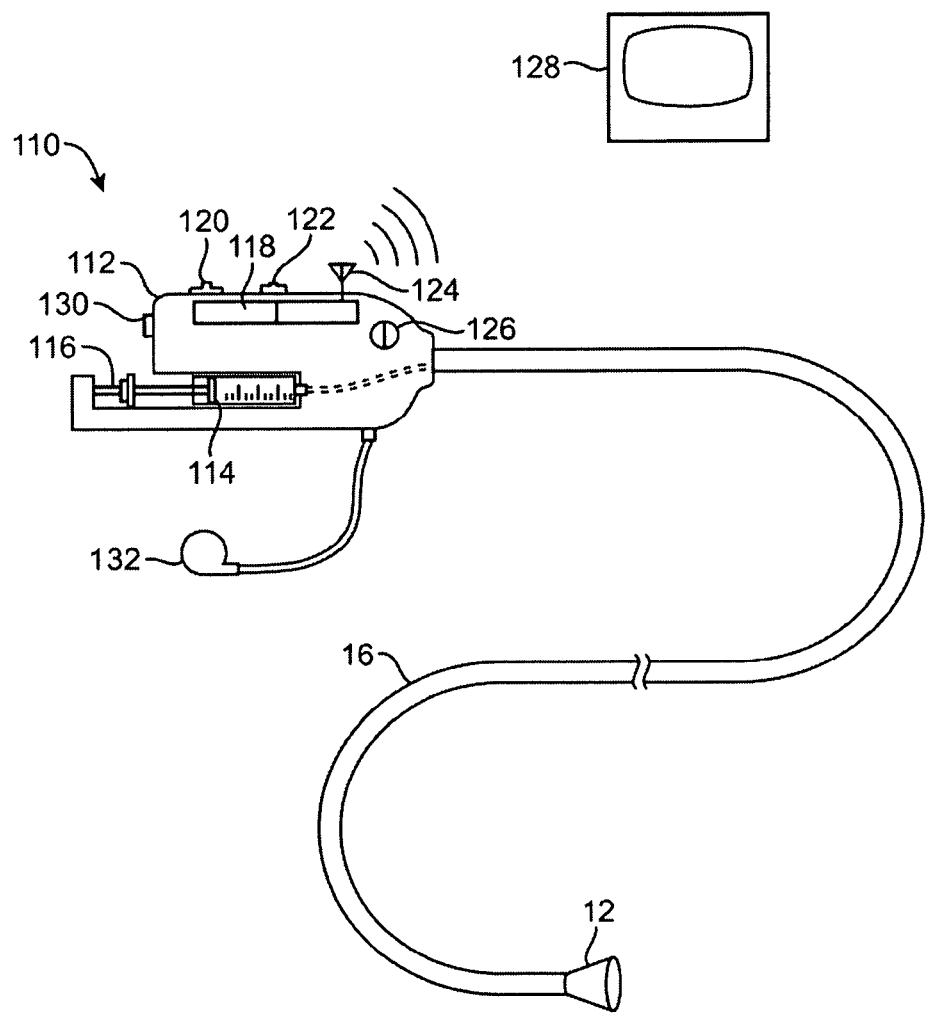
FIG. 8B shows a further illustration of a hand-held variation of the fluid delivery and tissue manipulation system.

FIG. 8B shows a further illustration of a hand-held variation of the fluid delivery and tissue manipulation system 110. In this variation, system 110 may have a housing or handle assembly 112 which can be held or manipulated by the physician from outside the patient body. The fluid reservoir 114, shown in this variation as a syringe, can be fluidly coupled to the handle assembly 112 and actuated via a pumping mechanism 116, e.g., lead screw. Fluid reservoir 114 may be a simple reservoir separated from the handle assembly 112 and fluidly coupled to handle assembly 112 via one or more tubes. The fluid flow rate and other mechanisms may be metered by the electronic controller 118.

Deployment of imaging hood 12 may be actuated by a hood deployment switch 120 located on the handle assembly 112 while dispensation of the fluid from reservoir 114 may be actuated by a fluid deployment switch 122, which can be electrically coupled to the controller 118. Controller 118 may also be electrically coupled to a wired or wireless antenna 124 optionally integrated with the handle assembly 112, as shown in the figure. The wireless antenna 124 can be used to wirelessly transmit images captured from the imaging hood 12 to a receiver, e.g., via Bluetooth® wireless technology (Bluetooth SIG, Inc., Bellevue, Wash.), RF, etc., for viewing on a monitor 128 or for recording for later viewing.

Articulation control of the deployment catheter 16, or a delivery catheter or sheath 14 through which the deployment catheter 16 may be delivered, may be accomplished by computer control, as described above, in which case an additional controller may be utilized with handle assembly 112. In the case of manual articulation, handle assembly 112 may incorporate one or more articulation controls 126 for manual manipulation of the position of deployment catheter 16. Handle assembly 112 may also define one or more instrument ports 130 through which a number of intravascular tools may be passed for tissue manipulation and treatment within imaging hood 12, as described further below. Furthermore, in certain procedures, fluid or debris may be sucked into imaging hood 12 for evacuation from the patient body by optionally fluidly coupling a suction pump 132 to handle assembly 112 or directly to deployment catheter 16.

Figure 9A:
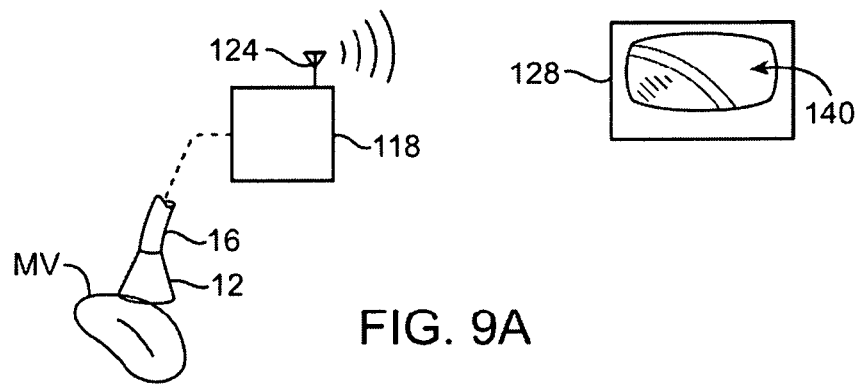
FIGS. 9A to 9C illustrate an example of capturing several images of the tissue at multiple regions.
Figure 9B:
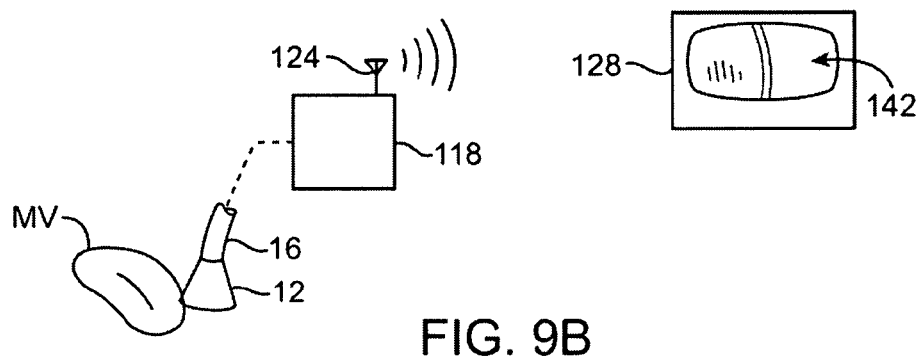
Figure 9C:
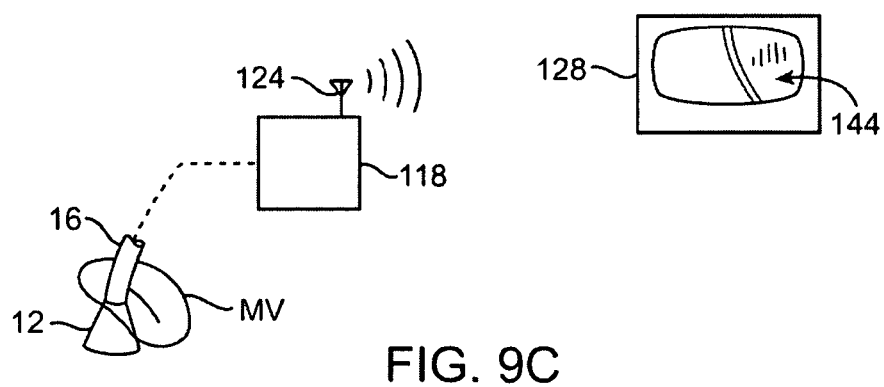

As described above, fluid may be pumped continuously into imaging hood 12 to provide for clear viewing of the underlying tissue. Alternatively, fluid may be pumped temporarily or sporadically only until a clear view of the tissue is available to be imaged and recorded, at which point the fluid flow may cease and the blood may be allowed to seep or flow back into imaging hood 12. FIGS. 9A to 9C illustrate an example of capturing several images of the tissue at multiple regions. Deployment catheter 16 may be desirably positioned and imaging hood 12 deployed and brought into position against a region of tissue to be imaged, in this example the tissue surrounding a mitral valve MV within the left atrium of a patient's heart. The imaging hood 12 may be optionally anchored to the tissue, as described above, and then cleared by pumping the imaging fluid into the hood 12. Once sufficiently clear, the tissue may be visualized and the image captured by control electronics 118. The first captured image 140 may be stored and/or transmitted wirelessly 124 to a monitor 128 for viewing by the physician, as shown in FIG. 9A.

The deployment catheter 16 may be then repositioned to an adjacent portion of mitral valve MV, as shown in FIG. 9B, where the process may be repeated to capture a second image 142 for viewing and/or recording. The deployment catheter 16 may again be repositioned to another region of tissue, as shown in FIG. 9C, where a third image 144 may be captured for viewing and/or recording. This procedure may be repeated as many times as necessary for capturing a comprehensive image of the tissue surrounding mitral valve MV, or any other tissue region. When the deployment catheter 16 and imaging hood 12 is repositioned from tissue region to tissue region, the pump may be stopped during positioning and blood or surrounding fluid may be allowed to enter within imaging hood 12 until the tissue is to be imaged, where the imaging hood 12 may be cleared, as above.

As mentioned above, when the imaging hood 12 is cleared by pumping the imaging fluid within for clearing the blood or other bodily fluid, the fluid may be pumped continuously to maintain the imaging fluid within the hood 12 at a positive pressure or it may be pumped under computer control for slowing or stopping the fluid flow into the hood 12 upon detection of various parameters or until a clear image of the underlying tissue is obtained. The control electronics 118 may also be programmed to coordinate the fluid flow into the imaging hood 12 with various physical parameters to maintain a clear image within imaging hood 12.

Figure 10:
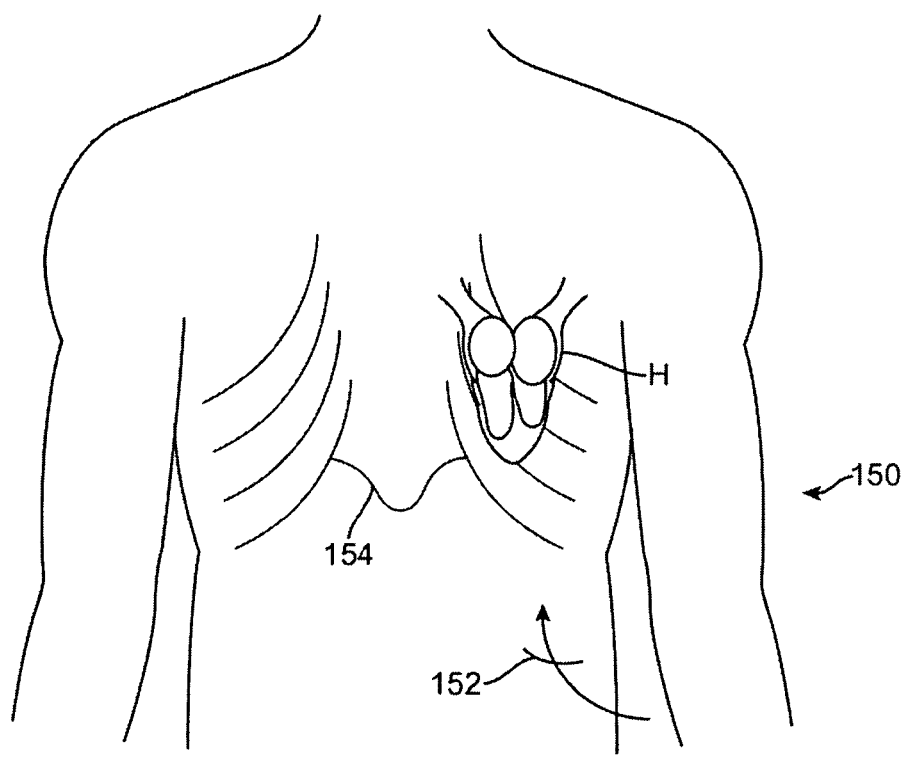
FIG. 10 illustrates a subxiphoid approach through a percutaneous incision inferior to the xiphoid process through which the visualization catheter may be advanced to percutaneously access regions within the body, such as the heart.

Aside from intravascular approaches for accessing regions within the body for treatment, alternative approaches may include a percutaneous surgical approach utilizing the apparatus and systems described herein for treating regions, e.g., within the heart to provide real-time in vivo images of tissue. An example of such a percutaneous approach may include advancement of a device via a subxiphoid or trans-thoracic approach. As illustrated in FIG. 10, a subxiphoid approach 150 is shown where a percutaneous incision 152 inferior to the xiphoid process 154 may be made in a patient body for accessing, e.g., the heart H to affect a treatment.

Figure 11A:
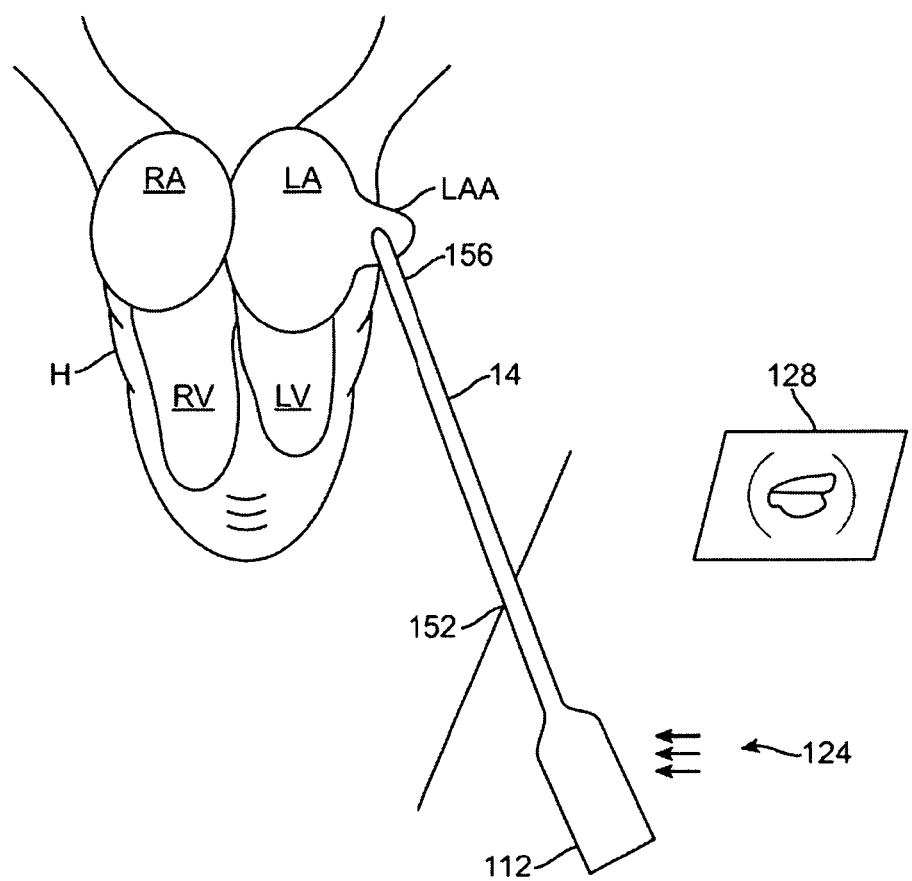
FIGS. 11A and 11B illustrate one example where the steerable/articulatable portion of the sheath may be inserted through a percutaneous incision and advanced towards the left atrial appendage for accessing the interior chambers of the heart.
Figure 11B:
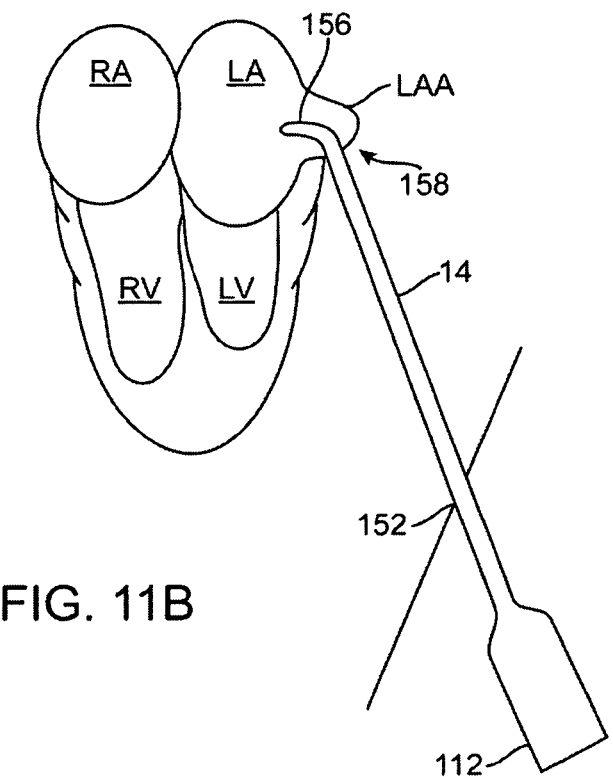

FIG. 11A illustrates one example where the steerable/articulatable portion 156 of sheath 14 may be inserted through incision 152 and advanced towards the left atrial appendage LAA extending from the heart H adjacent to the left atrium LA. Sheath 14 may be manipulated via handle assembly 112 from outside the incision 152 and the integrated imaging assembly may transmit, e.g., wirelessly 124, to a monitor 128 the visual images of the tissue during advancement and positioning of sheath 14 for viewing by the physician.

With the distal portion of sheath 156 positioned adjacent to the external surface of the left atrial appendage LAA, an incision 158 may be made along a portion of the left atrial appendage LAA to provide an entry pathway for sheath 14 into the interior chambers of the heart H, as shown in FIG. 1/ B. Incision 158 may be made by a piercing instrument or energized probe passed through sheath 14 or advanced through a separate sheath introduced through a separate subxiphoid or intercostal incision. In either case, once incision 156 has been made, sheath 14 may be carefully introduced therethrough and advanced into the left atrium LA of the heart H.

Figures 12A, 12B:
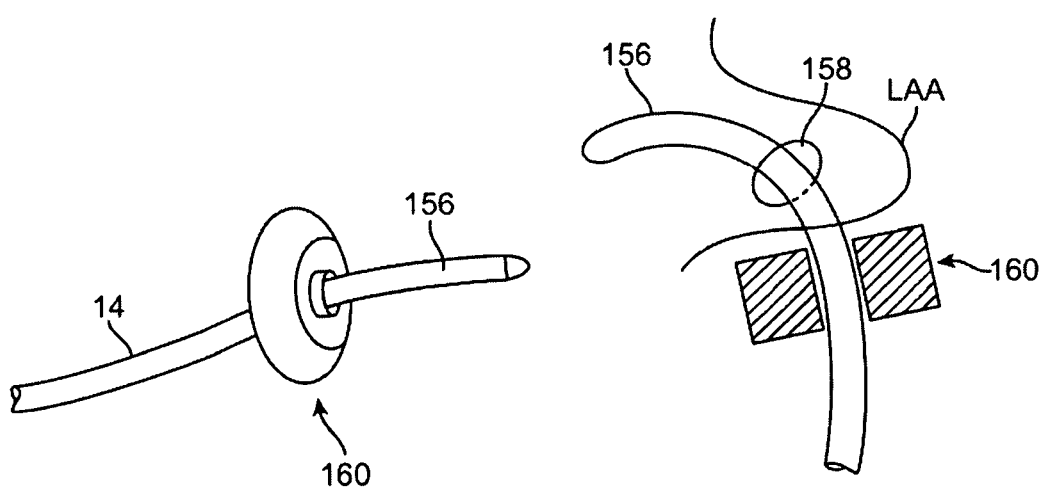
FIGS. 12A and 12B show perspective and partial cross-sectional views, respectively, of a sheath having an inflatable or expandable member for placement against the opening through the left atrial appendage to maintain a seal around the entry incision into the heart.

With sheath 14 passing through the left atrial appendage LAA, an expandable seal may be positioned around the opening of incision 158 to maintain hemostasis and inhibit or prevent tissue tearing and blood loss during the procedure. One example may include an expandable seal 160 which may inflate or otherwise expand along sheath 14 proximal to the steerable portion 156 of sheath 14, as shown in the perspective view of FIG. 12A. Seal 160 may be expanded from a low-profile configuration during delivery and then expanded once positioned proximal to incision 158 and left atrial appendage LAA, where it may be placed against incision 158, as shown in the partial cross-sectional view of FIG. 12B. Thus, seal 160 may be configured as an inflatable balloon expanded via a fluid or gas through an inflation lumen defined along sheath 14. Alternatively, seal 160 may be configured as a foam washer that could slide concentrically around the outside of sheath 14 to reduce blood loss after penetrating the left atrial appendage. The foam washer could slide along sheath 14 and form a temporary clot and therefore seal around the circumference of the sheath 14 against incision 158.

Figure 13A:
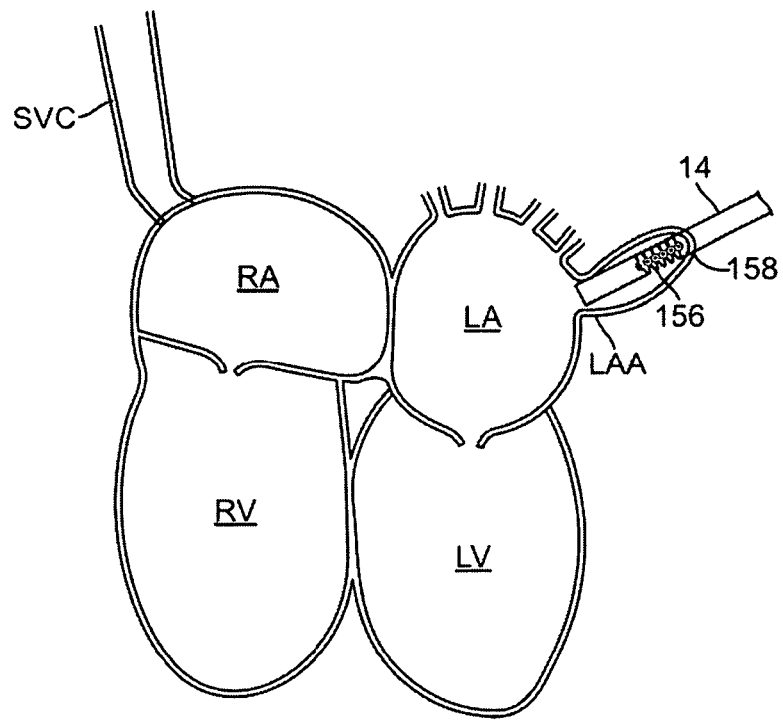
FIGS. 13A and 13B illustrate one method where the sheath may be advanced into the heart through the left atrial appendage for visualization and/or treatment.
Figure 13B:
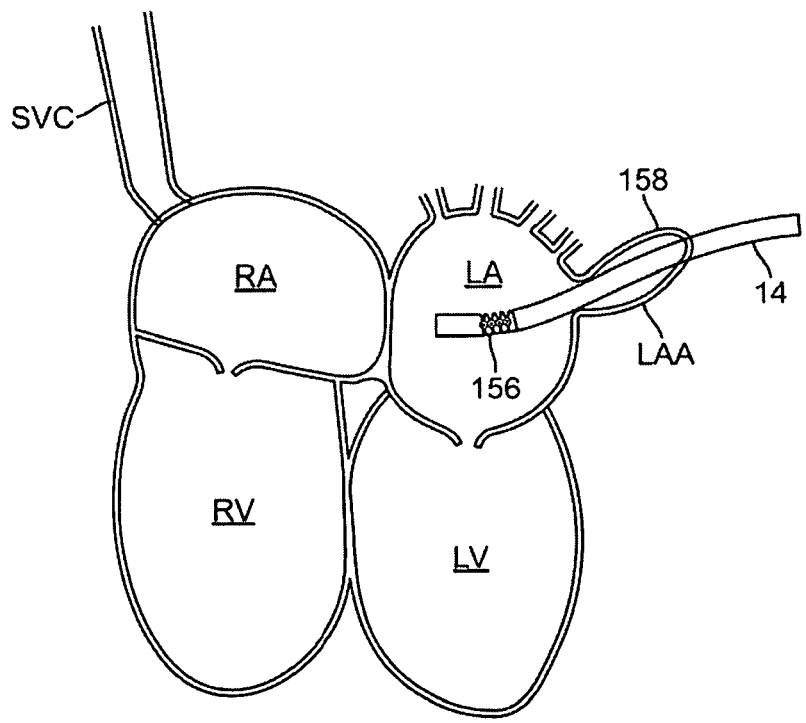

Once sheath 14 has been advanced into and through the left atrial appendage LAA, as shown in the partial cross-sectional view of FIG. 13A, sheath 14 may be steered or manipulated further into the left atrium LA of the heart H where any number of procedures may be affected within the left atrium LA, as shown in FIG. 13B, or any of the other chambers. The optional steerable portion 156 of the sheath 14 may be articulated to facilitate advancement of sheath 14 in any number of directions. Although shown entering the heart interior via the left atrial appendage LAA, other trans-cardiac points of entry may also be utilized as desired.

Figure 14A:
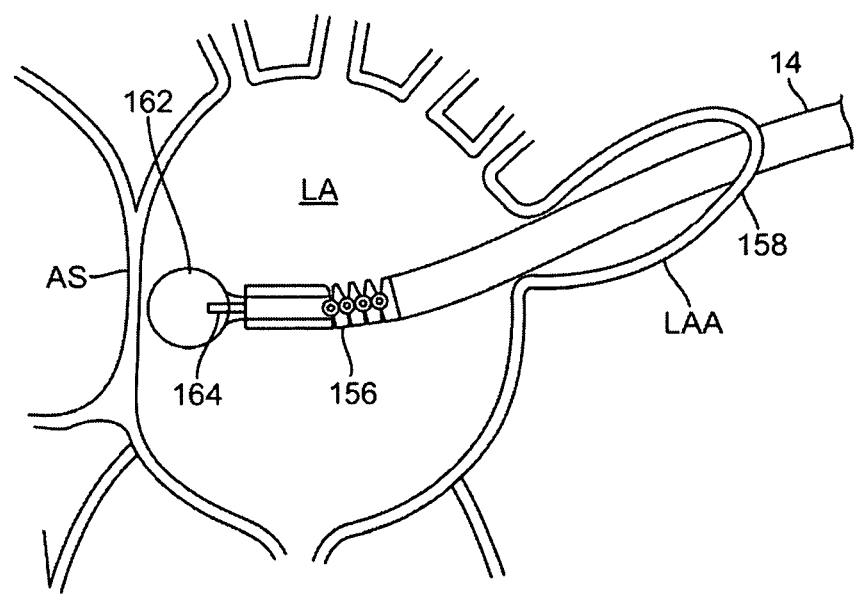
FIG. 14A shows an inflatable balloon for placement against the atrial septum to provide the user an initial visual determination of the position of the catheter distal end prior to expansion of the visualization imaging hood.

In one example, the assembly may be advanced towards the atrial septum AS to access the right atrium RA through the septal wall. As the distal end of sheath 14 is positioned adjacent to the atrial septum AS, an inflatable balloon 162 may be deployed from the distal end of sheath 14 and expanded with a translucent fluid or gas, including any of the fluids described above. In this example, an imager (e.g., optical fibers, CCD or CMOS imager) may be positioned within the balloon 162 for imaging therethrough such that as the sheath 14 distal end is initially positioned proximate to the septal tissue wall, the balloon 162 may be placed against the tissue surface to provide the user an initial visual determination of a position of the catheter distal end prior to expansion of the visualization imaging hood 12, as shown in FIG. 14A. Accordingly, a contrast agent may be optionally utilized to fill the balloon to provide for further visualization in addition to an optional extra-corporeal visual modality, e.g., fluoroscopy, ultrasound, etc. With balloon 162 inflated and pressed against the atrial septum AS, the underlying tissue may be viewed to determine whether the tissue region is a suitable location for transseptally puncturing through the septum. Otherwise, the balloon 162 may be optionally deflated and sheath 14 repositioned along another location or balloon 162 may be moved along the tissue wall in its inflated state until a suitable location has been found.

Figure 14B:
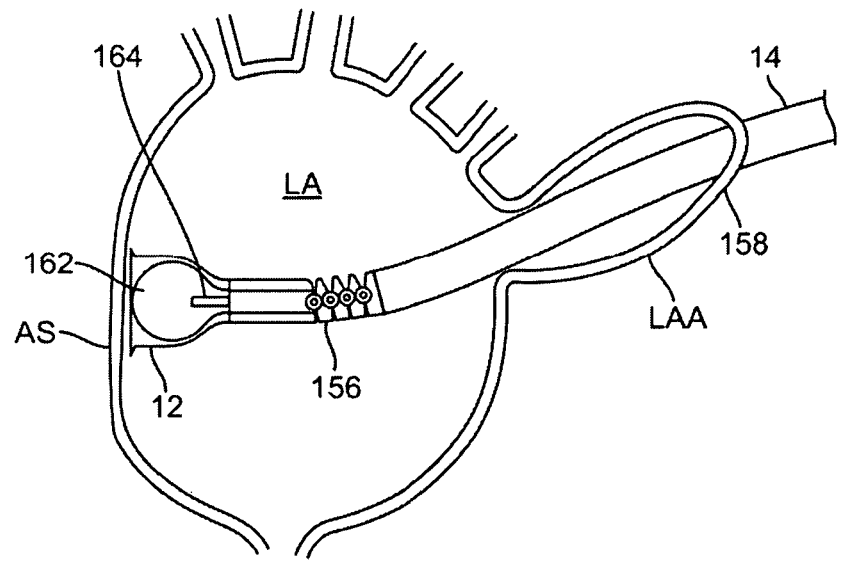
FIGS. 14B and 14C illustrate the inflatable balloon and the imaging hood deployed with an imaging element disposed within and proximal to the balloon, respectively.
Figure 14C:
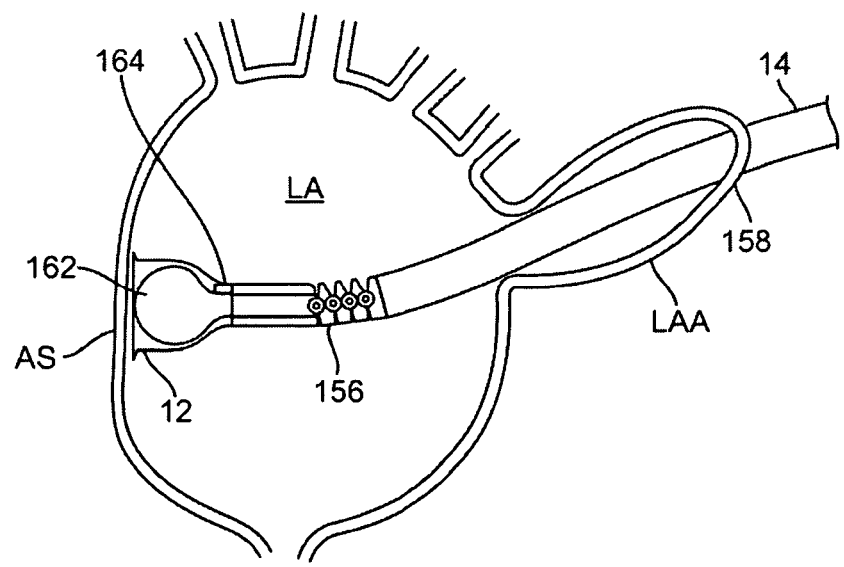

Once a desirable location has been found along the atrial septum AS, balloon 162 may be deflated and hood 12 may be deployed against the tissue surface. Alternatively, imaging hood 12 may be expanded and deployed around the balloon 162 or the balloon 162 may be initially expanded with hood 12 already expanded. In either case, once hood 12 is expanded and positioned against the tissue, balloon 162 may be deflated and optionally removed to clear the open area within hood 12 for advancement of instruments therethrough. In any of these variations, the imaging element 164 may be positioned within balloon 162, as shown in FIG. 14B, or adjacent and proximal to balloon 162, as shown in FIG. 14C.

Figure 15:
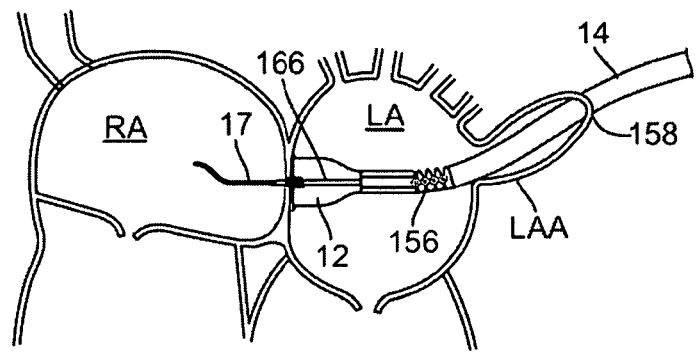
FIG. 15 shows one example where a guidewire may be passed transseptally through the atrial septum via a piercing instrument deployed from the catheter for accessing the right atrium.
Figure 16:
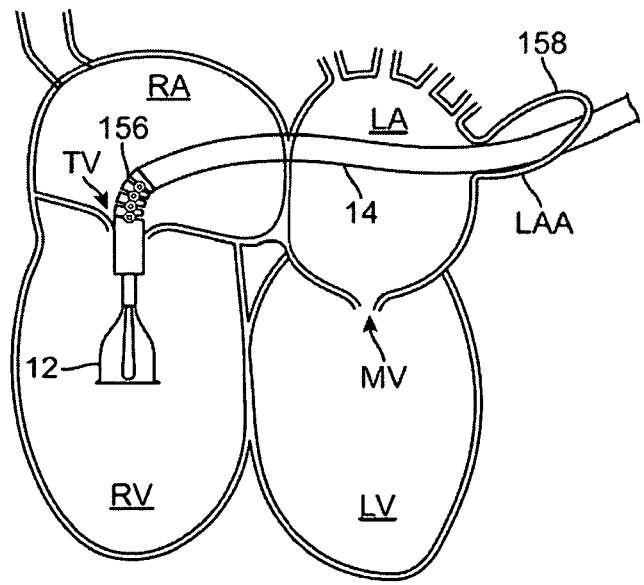
FIG. 16 shows an example where the imaging hood may be further advanced into the right ventricle via the right atrium through the tricuspid valve.

With balloon 162 deflated or otherwise cleared, a piercing instrument 166, such as a needle, may be advanced through hood 12 and through the atrial septum AS while under direct visualization. With the distal tip of piercing instrument 166 pierced through the septal wall, guidewire 17 may be passed through a lumen defined through the needle 166 and advanced into the body lumen, such as the right atrium RA, as shown in FIG. 15. Alternatively, hood 12 in its collapsed configuration may be passed through the septal wall entirely where hood 12 may then be expanded within the right atrium RA for treatment upon the tissue therewithin. Additionally or optionally, hood 12 may be collapsed again within the right atrium RA or it may be passed while remaining in its collapsed configuration through the tricuspid valve TV between the right atrium RA and right ventricle RV. Once the distal end of sheath 14 has been passed through the tricuspid valve TV, hood 12 may be expanded and articulated, for instance, via the steerable portion 156 to directly visualize and/or treat tissue regions within the right ventricle RV, as shown in FIG. 16.

Figure 17A:
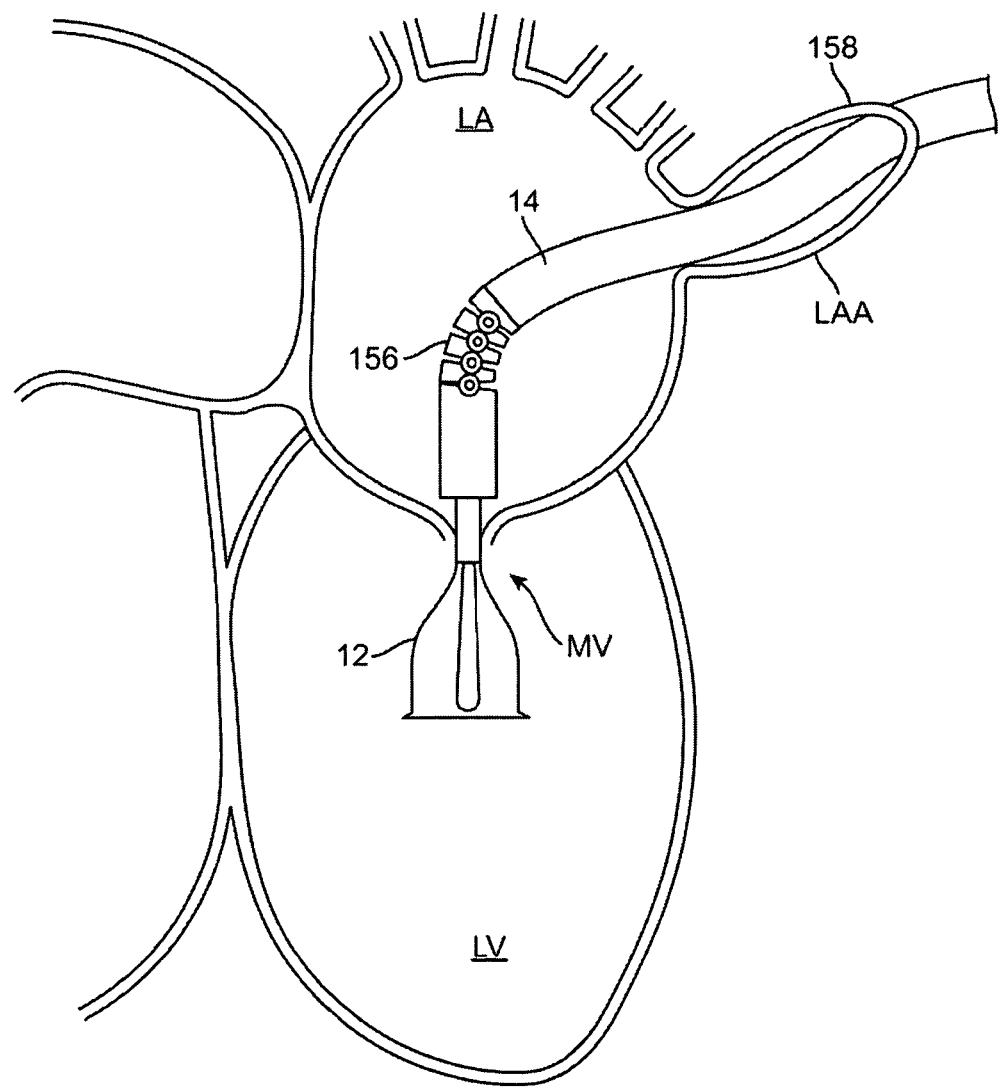
FIG. 17A shows an example where the imaging hood may be advanced through the mitral valve and into the left ventricle.

Alternatively, sheath 14 may be articulated to pass imaging hood 12 in its collapsed configuration through the mitral valve MV in order to access the left ventricle LV, where hood 12 may then be deployed for visualizing and/or treating regions of tissue therewithin, as shown in FIG. 17A. In yet another alternative, once hood 12 has been advanced through incision 158 within the left atrial appendage LAA, hood 12 may be articulated or steered towards the pulmonary veins for visualization and/or treatment thereof, for example, for atrial fibrillation.

Figure 17B:
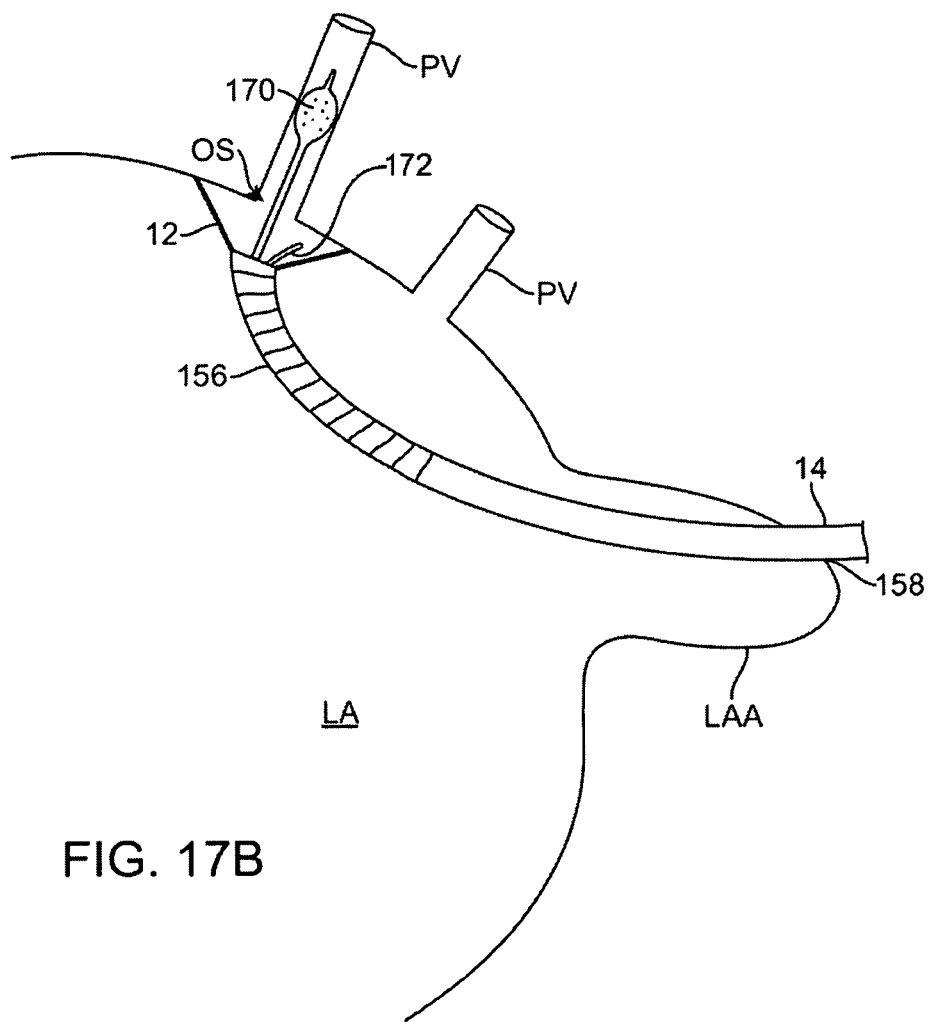
FIG. 17B shows another example where the imaging hood and an occlusion balloon may be directed into a pulmonary vein for treating the tissues surrounding the ostium, e.g., for atrial fibrillation.

As shown in FIG. 17B, the imaging hood 12 may be expanded and advanced towards one of the ostia OS of the pulmonary veins PV. An occlusion member 170, such as an inflatable balloon, may be advanced through the catheter, past the ostium OS, and into a portion of the pulmonary vein PV, where the occlusion member 170 may be expanded to completely or at least partially occlude the blood flow. Once the blood flow through the vessel has been sufficiently occluded or reduced, an ablation catheter 172 may be deployed through the hood 12 and actuated to ablate the tissue region around the ostium OS while under direct visualization within hood 12, for example, to create a conduction block for treating atrial fibrillation. Moreover, with the blood flow occluded or reduced, the region may be optionally infused temporarily with the translucent fluid, such as saline, to clear the visual field to perform the ablation procedure, if necessary or desired.

Figure 18:
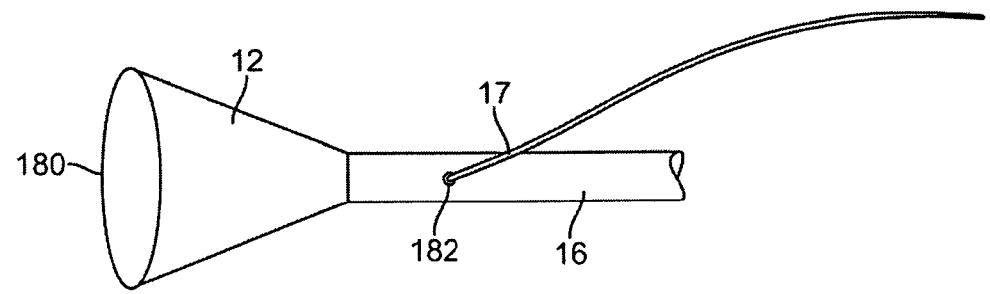
FIG. 18 illustrates an example where a guidewire exchange lumen may be defined along the catheter proximally of the hood for rapid exchange.

In yet additional variations, to facilitate use of the devices for any of the procedures described herein, hood 12 may be integrated with one or more angled projections 180 extending distally from hood 12, as shown in FIG. 18. Once hood 12 is contacted against a tissue region, projections 180 may be engaged into the tissue by rotating catheter shaft 16 to temporarily secure the hood 12 against the tissue surface. Disengagement may be accomplished by simply rotating catheter shaft 16 in the opposite direction. Catheter shaft 16 may also additionally incorporate a guidewire exchange lumen 182 defined along catheter 16 proximally of hood 12. Lumen 182 may allow for the rapid exchange of devices, including the catheter 16 and hood 12, during an interventional procedure when utilized with guidewire 17.

Figure 19:
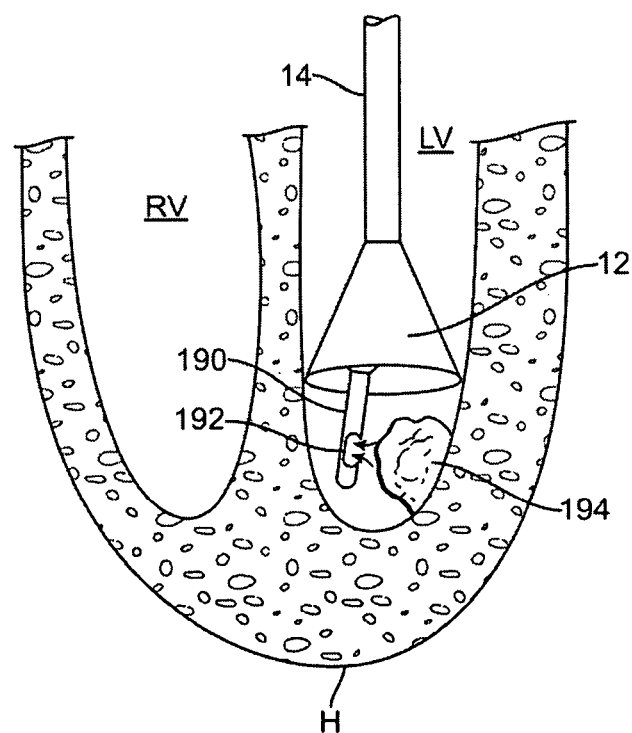
FIG. 19 illustrates an example in which a catheter may be utilized to remove emboli or debris under direct visualization within a chamber of the heart.

In yet another treatment, a thrombectomy-type catheter shaft 190 having an opening 192 defined along its outer surface may be advanced within the deployment catheter and through hood 12 for extracting and/or removing emboli or other debris 194 from within the heart chambers. As shown in FIG. 19, sheath 14 and hood 12 may be advanced and deployed within the left ventricle LV, as described above. With hood 12 expanded, it may be placed against a region of the tissue to isolate emboli 194 such that the translucent fluid may be introduced to clear the isolated region for direct visualization of the tissue and emboli 194. Once visually confirmed, catheter 190 may be advanced from hood 12 such that opening 192 is brought into contact against or adjacent to emboli 194. The debris may then be drawn into the catheter 190 for removal from the left ventricle LV while under direct visualization to confirm removal of the material. Although illustrated as removing material within the left ventricle LV, such extraction may be accomplished in any of the chambers of the heart as well as in other regions of the body as practicable.

Figures 20A, 20B:
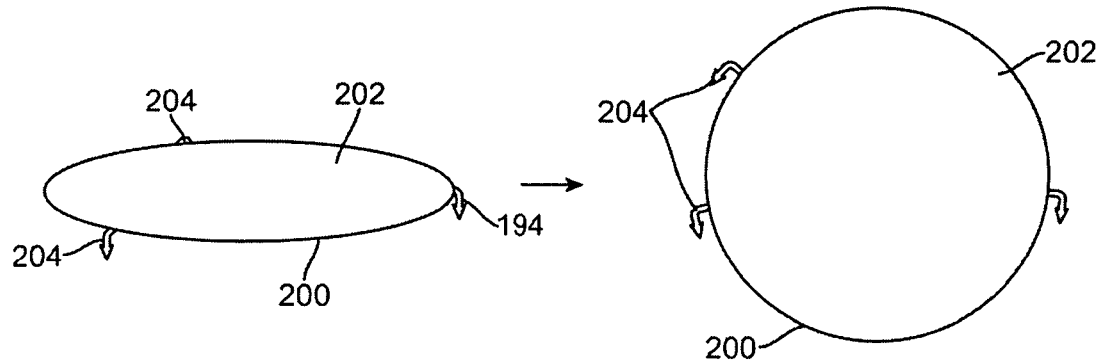
FIGS. 20A and 20B illustrate an example of a tissue defect closure device comprised of a shape memory or superelastic material which may be anchored to the tissue surrounding the defect via one or more anchors.
Figure 20C:
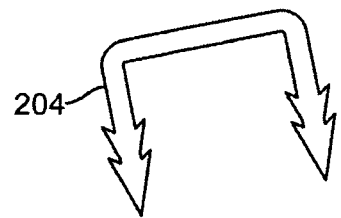
FIG. 20C shows a side view of an example of a dual-legged anchor which may be used to secure the closure device to the underlying tissue.

Aside from removal of debris, other procedures within the heart H may also be accomplished. For instance, closure of an opening or defect along the ventricular or atrial wall, e.g., patent foramen ovale (PFO), atrial septal defect (ASD), etc. may also be accomplished via the visualization catheter. FIGS. 20A and 20B illustrate an example of a device comprised of a shape memory or superelastic material, e.g., nickel-titanium alloy or Nitinol, in which rim 200 having a mesh or polymeric covering 202 supported by rim 200 may be configured to be delivered in a collapsed profile, as shown in FIG. 20A, when constrained within the delivery catheter. When deployed, a pusher may force or eject the rim 200 out of the catheter such that the structure may deploy into its expanded configuration, as shown in FIG. 20B. Although illustrated as having a circular expanded configuration, rim 200 may be configured alternatively into a number of different configurations (e.g., elliptical, triangular, rectangular, etc.) depending upon the anatomy of the opening or defect to be patched. Rim 200 may also have one or more anchoring legs 204, illustrated in FIG. 20C as a dual-legged clip, integrated with rim 200 or attached thereto to secure the structure to the underlying tissue surrounding the defect. Rim 200 and anchoring legs 204 may be delivered through the catheter and passed into hood 12, e.g., via a pusher or grasper, where it may be advanced into the underlying tissue while under direct visualization within hood 12.

Figure 21A:
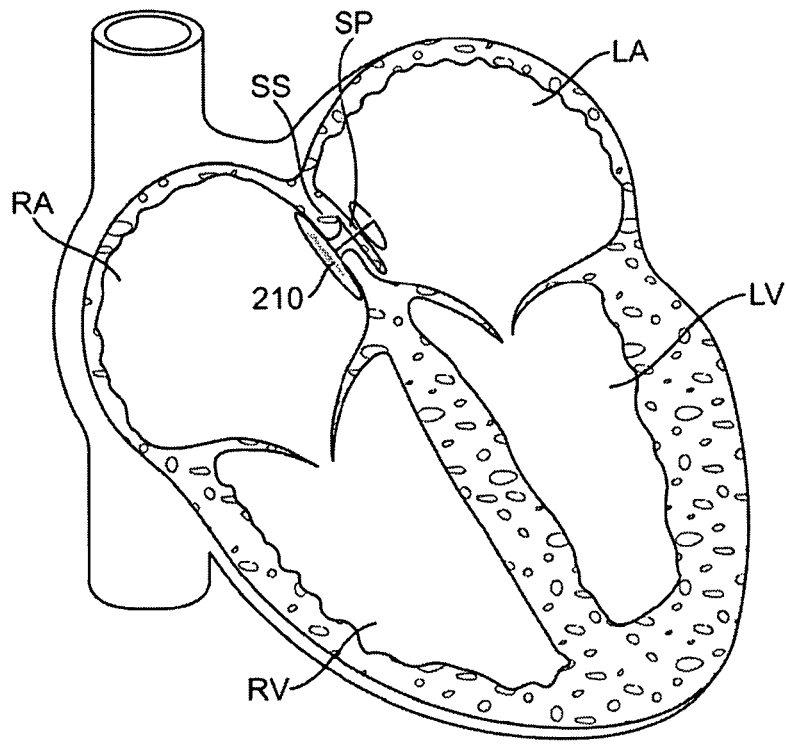
FIG. 21A illustrates a partial cross-sectional view of a closure device placed within an atrial defect to occlude the opening.
Figure 21B:
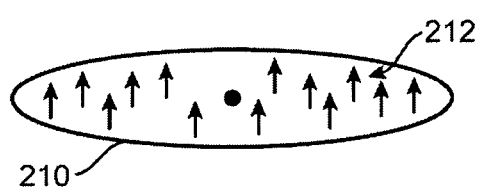
FIGS. 21B and 21C illustrate perspective views of another closure device comprising a patch with a plurality of anchors extending from a surface of the patch for securement against the underlying tissue.
Figure 21C:
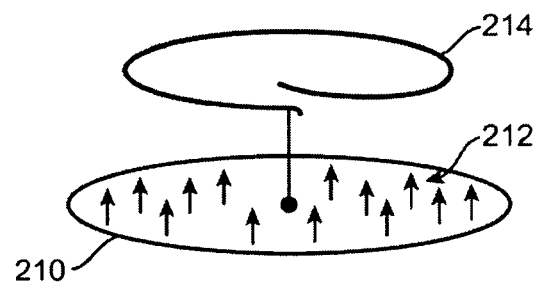
Figure 21D:
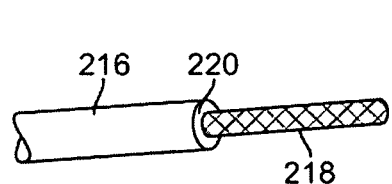
FIGS. 21D and 21E illustrate an expandable mesh attached to a delivery member in its collapsed delivery profile when contained within a catheter and in its expanded profile, respectively.
Figure 21E:
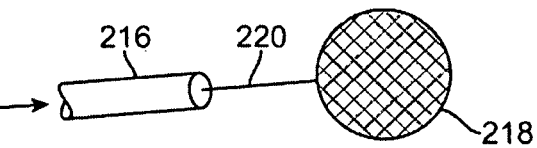

In another variation of a PFO or ASD closure device, FIGS. 21B and 21C illustrate perspective views of another closure device 210 comprising a patch, as above, with a plurality of anchors 212 extending from a surface of the patch for securement against the underlying tissue. Closure device 210 may also comprise a locking mechanism 214 extending from device 210 and forming an expanded structure for placement through the defect and expansion on an opposite side of the tissue wall to prevent or inhibit the movement or displacement of the closure device 210 from the defect, as shown in FIG. 21A. An expandable mesh 218 attached to a delivery member 220 may also be seen in its collapsed delivery profile when contained within catheter 216, as shown in FIG. 21D, and in its expanded profile, as shown in FIG. 21E, which could also be used between the tissue layers to close off the passage. Expandable mesh 218 may be advanced through a catheter lumen and expanded within or distal to hood 12 for placement within the defect while under direct visualization to facilitate the procedure or to obtain visual confirmation of secure placement. Such a closure device 218 and methods for using the same are intended to be illustrative and not limiting.

Accordingly, other intra-cardiac closure devices, as known in the art, may be utilized with the devices and methods described herein. For instance, closure devices and methods as shown in U.S. Pat. No. 3,874,388 (King et al.), which is incorporated herein by reference in its entirety, may also be utilized with the devices and methods described herein in yet another variation.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method for percutaneously accessing a region of tissue within a body, comprising:
   introducing a flexible deployment catheter through a percutaneous incision of the body and into a body lumen, the catheter having a distal end;
   positioning an imaging hood projecting distally from the deployment catheter into proximity to a region of tissue to be imaged within the body lumen;
   releasing the hood from within a sheath such that the hood reconfigures from a constrained state within the sheath to an expanded unconstrained state external to the sheath, wherein releasing the hood comprises self-expanding the hood when in the unconstrained state external to the sheath and wherein in the expanded unconstrained state, the imaging hood has a minimum diameter at a proximal opening interfaced with the distal end of the catheter and has maximum diameter at a distal opening, the imaging hood defining an open area between the proximal and distal openings;
   expanding an expandable seal around the sheath proximal to a distal end of the sheath;
   placing the distal opening against the region of tissue to be imaged;
   urging a translucent fluid into the hood via the deployment catheter such that an opaque fluid is displaced from within the hood and through the distal opening to an environment external to the hood; and
   visualizing the region of tissue through the translucent fluid via an imaging element positioned within the open area defined by the imaging hood in the expanded unconstrained state.

2. The method of claim 1 wherein introducing a deployment catheter further comprises advancing the catheter into a second incision along an outer surface of the body lumen.

3. The method of claim 2 further comprising, expanding the seal against the second incision to inhibit or prevent fluids from leaking therefrom.

4. The method of claim 2 wherein advancing the catheter comprises advancing a distal end of the catheter through the second incision along a left atrial appendage and into a left atrial chamber of a heart.

5. The method of claim 4 further comprising advancing the catheter towards an ostium of a pulmonary vein.

6. The method of claim 4 further comprising advancing the catheter through a mitral valve and into a left ventricular chamber.

7. The method of claim 4 further comprising advancing the catheter transseptally through an atrial septum and into a right atrial chamber.

8. The method of claim 7 further comprising advancing the catheter through a tricuspid valve and into a right ventricular chamber.

9. The method of claim 1 wherein positioning an imaging hood comprises articulating the flexible deployment catheter from outside the body to position the hood into proximity.

10. The method of claim 1 wherein positioning an expanded imaging hood comprises stabilizing a position of the hood relative to the tissue.

11. The method of claim 1 wherein urging a translucent fluid comprises pumping the translucent fluid into the hood through a fluid delivery lumen defined through the deployment catheter.

12. The method of claim 1 wherein urging a translucent fluid comprises urging saline, plasma, water, or perfluorinated liquid into the hood such that blood is displaced from the hood.

13. The method of claim 1 wherein visualizing the region of tissue further comprises illuminating the region of tissue.

14. The method of claim 1 further comprising treating the region of tissue with a therapeutic tool advanced through the deployment catheter.

15. The method of claim 1 further comprising placing an inflatable balloon distal to or within the imaging hood against the region of tissue and viewing therethrough prior to urging a translucent fluid into the hood.

16. The method of claim 1 further comprising deploying an implantable member onto the region of tissue.

17. The method of claim 1 further comprising extracting debris or emboli through the imaging hood.

18. The method of claim 1 wherein self-expanding the hood comprises self-expanding the hood via one or more superelastic support members.

19. A method for percutaneously accessing a region of tissue within a heart, comprising:
   introducing a flexible deployment catheter through a percutaneous incision of a body, the catheter having a distal end;
   advancing the deployment catheter proximate to an external surface of a left atrial appendage;
   inserting the deployment catheter through a second incision along the left atrial appendage into a left atrial chamber within the heart;
   positioning an imaging hood projecting distally from the deployment catheter into proximity to a region of tissue within the heart to be imaged;
   releasing the hood from within a sheath such that the hood reconfigures from a constrained state within the sheath to an expanded unconstrained state external to the sheath, wherein releasing the hood comprises self-expanding the hood when in the unconstrained state external to the sheath and wherein in the expanded unconstrained state, the imaging hood has a minimum diameter at a proximal opening interfaced with the distal end of the catheter and has maximum diameter at a distal opening, the imaging hood defining an open area between the proximal and distal openings;
   expanding an expandable seal around the sheath proximal to a distal end of the sheath;
   placing the distal opening against the region of tissue to be imaged;
   urging a translucent fluid into the hood via the deployment catheter such that blood is displaced from within the hood and through the distal opening to an environment external to the hood; and
   visualizing the region of tissue within the heart through the translucent fluid via an imaging element positioned within open area defined by the imaging hood in the expanded unconstrained state.

20. The method of claim 19 wherein inserting the deployment catheter further comprises expanding the expandable seal to form a seal against the second incision to inhibit or prevent fluids from leaking therefrom.

21. The method of claim 19 wherein inserting the deployment catheter further comprises advancing the catheter towards an ostium of a pulmonary vein.

22. The method of claim 19 wherein inserting the deployment catheter further comprises advancing the catheter through a mitral valve and into a left ventricular chamber.

23. The method of claim 19 wherein inserting the deployment catheter further comprises advancing the catheter transseptally through an atrial septum and into a right atrial chamber.

24. The method of claim 23 further comprising advancing the catheter through a tricuspid valve and into a right ventricular chamber.

25. The method of claim 19 wherein positioning an imaging hood comprises articulating the flexible deployment catheter from outside the body to position the hood into proximity to the region of tissue.

26. The method of claim 19 wherein visualizing a region of tissue further comprises stabilizing a position of the hood relative to the tissue.

27. The method of claim 19 wherein visualizing a region of tissue further comprises positioning the imaging hood projecting distally from the deployment catheter against the region of tissue to be imaged.

28. The method of claim 27 wherein urging a translucent fluid into the hood comprises urging saline into the hood.

29. The method of claim 28 wherein urging a translucent fluid comprises pumping the translucent fluid into the hood through a fluid delivery lumen defined through the deployment catheter.

30. The method of claim 28 further comprising placing an inflatable balloon distal to or within the imaging hood against the region of tissue and viewing therethrough prior to urging a translucent fluid into the hood.

31. The method of claim 19 further comprising treating the region of tissue with a therapeutic tool advanced through the deployment catheter.

32. The method of claim 19 further comprising deploying an implantable member onto the region of tissue.

33. The method of claim 32 wherein deploying comprises securing an expandable occlusion member into a septal defect.

34. The method of claim 19 further comprising extracting debris or emboli through the imaging hood.

35. The method of claim 19 wherein self-expanding the hood comprises self-expanding the hood via one or more superelastic support members.

* * * * *